United States Patent
Henn et al.

(10) Patent No.: US 8,536,398 B2
(45) Date of Patent: Sep. 17, 2013

(54) METHOD FOR PURIFYING SUPPLY FLOWS CONTAINING AROMATES BY MEANS OF ZEOLITES

(75) Inventors: Rolf Henn, Oftersheim (DE); Ulrich Müller, Neustadt (DE); Ferdinand Straub, Hockenheim (DE); Jürgen Dosch, Ludwigshafen (DE)

(73) Assignee: Styrolution GmbH (DE)

( * ) Notice: Subject to any disclaimer, the term of this patent is extended or adjusted under 35 U.S.C. 154(b) by 1902 days.

(21) Appl. No.: 11/663,326

(22) PCT Filed: Sep. 15, 2005

(86) PCT No.: PCT/EP2005/009909
§ 371 (c)(1),
(2), (4) Date: Mar. 20, 2007

(87) PCT Pub. No.: WO2006/032400
PCT Pub. Date: Mar. 30, 2006

(65) Prior Publication Data
US 2008/0139857 A1   Jun. 12, 2008

(30) Foreign Application Priority Data
Sep. 20, 2004  (DE) .......................... 10 2004 045 879

(51) Int. Cl.
*C07C 7/13*  (2006.01)
*C07C 2/66*  (2006.01)

(52) U.S. Cl.
USPC ........... 585/820; 585/823; 585/824; 585/448; 585/518; 585/519

(58) Field of Classification Search
USPC .................. 585/820, 823, 824, 448, 518, 519
See application file for complete search history.

(56) References Cited

U.S. PATENT DOCUMENTS

| | | | |
|---|---|---|---|
| 5,744,686 A * | 4/1998 | Gajda | 585/823 |
| 5,942,650 A | 8/1999 | Gajda | |
| 6,297,417 B1 | 10/2001 | Samson et al. | |
| 6,617,482 B1 * | 9/2003 | Venkat et al. | 585/448 |

FOREIGN PATENT DOCUMENTS

| | | |
|---|---|---|
| WO | WO-98/07673 | 2/1998 |
| WO | WO-00/35836 | 6/2000 |
| WO | WO-01/07383 | 2/2001 |

\* cited by examiner

*Primary Examiner* — Thuan D Dang
(74) *Attorney, Agent, or Firm* — Novak Druce Connolly Bove + Quigg LLP

(57) ABSTRACT

Processes suitable for purifying aromatic-containing feed streams, and processes using such purified streams are described, wherein the purification processes comprise: (a) providing a process feedstream comprising an aromatic component; and (b) bringing the process feedstream into contact with a first zeolite and a second zeolite; wherein the first zeolite has a mean pore size of 0.3 to 0.5 nm, and wherein the second zeolite has a mean pore size of 0.6 to 0.8 nm.

20 Claims, No Drawings

METHOD FOR PURIFYING SUPPLY FLOWS CONTAINING AROMATES BY MEANS OF ZEOLITES

CROSS-REFERENCE TO RELATED APPLICATIONS

This application is a national stage application, under 35 U.S.C. §371, of PCT/EP2005/009909, filed Sep. 15, 2005, which claims priority of German Application No. 10 2004 045 879.0, filed Sep. 20, 2004.

BACKGROUND OF THE INVENTION

The invention relates to a process for purifying feed streams comprising aromatics in polymerization or alkylation processes by bringing them into contact with zeolites, which comprises passing the feed stream over at least two zeolites 1 and 2, with zeolite 1 having a mean pore size of from 0.3 to 0.5 nm and zeolite 2 having a mean pore size of from 0.6 to 0.8 nm.

Alkylated aromatics are obtained predominantly by catalytic alkylation of aromatics by means of olefins: ethylbenzene, for example, by alkylation of benzene by means of ethylene, cumene, for example, by alkylation of benzene by means of propylene. Catalysts used in the liquid phase are aluminum chloride and catalysts used in the gas phase are Lewis acids or synthetic zeolites. Zeolites are highly active catalysts both for alkylation and for transalkylation. Since the zeolite catalysts are susceptible to water, sulfur and other catalyst poisons, they lose their activity over time and have to be regenerated periodically.

Various processes have been proposed for lengthening the life of zeolite catalysts for alkylation reactions. WO 98/07673 describes the alkylation of benzene by means of, for example, propylene. The benzene is pretreated by passing it over aluminum oxides, silicates, aluminum silicates or acidic zeolites such as mordenites.

WO 00/35836 describes a method which comprises firstly alkylating an aromatic, purifying the alkyl aromatic obtained by means of a molecular sieve and finally reacting the purified alkyl aromatic with another aromatic in a transalkylation reaction to give a monoalkylaromatic. Suitable molecular sieves are suitable zeolites and mixtures thereof, with acidic zeolites such as MCM-22 being preferred. However, it has now been found that the effectiveness of these acidic zeolites is unsatisfactory.

WO 01/07383 discloses the purification of feed streams comprising olefins in polymerization or alkylation processes by passing the olefin, e.g. ethylene, over an adsorption bed of carbon black, activated carbon, aluminum oxides, silicates, aluminum silicates, various zeolites or molecular sieves. It is stated that the benzene or alkyl benzene feed stream is advantageously passed over an appropriate adsorption bed comprising the adsorbents mentioned; further details are not given.

The purifying action of these processes for aromatics is not satisfactory in all cases, or expensive adsorbents are required.

BRIEF SUMMARY OF THE INVENTION

It was an object of the invention to provide an improved process for purifying aromatics, in particular aromatics which are to be used in a polymerization or alkylation process.

This purification process should increase the life of alkylation or transalkylation catalysts in the catalytic alkylation of aromatics by means of olefins, in particular over zeolite catalysts, and to reduce the need for regeneration.

We have accordingly found the process defined at the outset (hereinafter referred to as purification process). In addition, we have found a process (alkylation process) for preparing alkylated aromatics by reacting aromatics and olefins over a catalyst, wherein the feed stream comprising aromatics is pretreated by means of the purification process. Preferred embodiments of the invention are defined in the subordinate claims.

The purification process of the invention can in principle also be used for feed streams comprising aromatics in other processes. However, it is particularly useful for polymerization and alkylation processes, in particular ones in which catalysts which are sensitive to very small amounts of impurities are used.

DETAILED DESCRIPTION OF THE INVENTION

Aromatics suitable for purification include both unalkylated aromatics, e.g. those which can be reacted with an olefin in an alkylation reaction to give alkylated aromatics, and monoalkylated or polyalkylated aromatics which, for example, can be reacted with other aromatics in a transalkylation reaction to give other alkylated aromatics. Possible unalkylated aromatics are, for example, benzene and fused aromatics such as naphthalene or anthracene. Suitable alkylated aromatics are ones having from 1 to 10 carbon atoms in the alkyl radical, for example monoalkylated aromatics such as toluene or ethylbenzene or polyalkylated aromatics such as xylenes. Preference is given to using benzene as aromatic to be purified.

The aromatic is advantageously dewatered to a water content of less than 100 ppm by weight, preferably less than 30 ppm by weight (measured by the Karl Fischer method in accordance with DIN 51777), before being fed to the purification process. This is achieved in a customary manner, for example by means of drying columns when the process is carried out continuously.

According to the invention, the feed stream comprising aromatics is brought into contact with the zeolites by passing the feed stream over at least two zeolites 1 and 2. The terms zeolite 1 and zeolite 2 serve merely to distinguish the two zeolites from one another for making the text clearly understandable and do not imply any particular type of zeolite structure.

Zeolite 1 has a mean pore size of from 0.3 to 0.5 nm (3 to 5 Å), and zeolite 2 has a mean pore size of from 0.6 to 0.8 nm (6 to 8 Å). Accordingly, zeolite 1 has fine pores and zeolite 2 has medium to large pores.

In a preferred embodiment of the process, use is made of, based on the sum of zeolite 1 and zeolite 2,
a) from 10 to 90% by weight, preferably from 30 to 70% by weight and in particular from 40 to 60% by weight, of zeolite 1, and
b) from 10 to 90% by weight, preferably from 30 to 70% by weight and in particular from 40 to 60% by weight, of zeolite 2.

In a likewise preferred embodiment, zeolite 1 has a mean pore size of from 0.38 to 0.42 nm (3.8 to 4.2 Å), in particular about 0.4 nm (4 Å) and zeolite 2 has a mean pore size of from 0.68 to 0.72 nm (6.8 to 7.2 Å), in particular about 0.7 nm (7 Å).

Suitable zeolites 1 are, for example, zeolites of the structure type LTA having pore sizes of from 0.3 to 0.5 nm. Particularly preferred zeolites 1 having pore sizes of about 0.4 nm are LTA zeolites in the sodium form.

Suitable zeolites 2 are, for example, zeolites of the structure type FAU having pore sizes of from 0.6 to 0.8 nm. Particularly preferred zeolites 2 having pore sizes of about 0.7 nm are FAU zeolites in the sodium form or calcium form.

The zeolites 1 and 2 used are preferably not acidic or acid-activated zeolites. Particular preference is given to using neutral zeolites 1 and 2.

It goes without saying that mixtures of a plurality of zeolites 1', 1", etc., can also be used as zeolite 1 and mixtures of various zeolites 2', 2", etc., can also be used as zeolite 2.

The zeolites mentioned are known and are commercially available. Structure, properties and preparation of zeolites are described, for example, in Zeolite Molecular Sieves, Donald W. Breck, John Wiley & Sons, 1974; in Atlas of Zeolite Framework Types, Ch. Baerlocher/W. M. Meier/D. H. Olson, 5th Ed., Elsevier 2001; or in Handbook of Molecular Sieves, R. Szostak, Chapman & Hall, New York, 1992.

In general, the zeolites are used in the form of spheres, rods or granules having an external dimension of from 0.5 to 10 mm.

In the process of the invention, the zeolites can be present as a fixed, moving or fluidized bed. The zeolites are preferably present as a fixed bed. The zeolites 1 and 2 can be mixed and this mixture can be used as fixed, moving or fluidized bed, or, and this is preferred, zeolite 1 and zeolite 2 can be arranged separately from one another in different beds, with the beds being arranged one after the other (in series) and being able to be, independently of one another, fixed, moving or fluidized. Preference is given to both zeolite 1 and zeolite 2 being present as a fixed bed.

It goes without saying that each bed can also be configured as a plurality of successive beds.

The process of the invention can be carried out batchwise or continuously. The configuration in terms of apparatus of the zeolite bed or beds is the customary configuration; for example, the zeolite bed can be located in an absorber or another suitable vessel through which the aromatic to be purified flows. Preference is given to using fixed-bed absorbers. The absorber or other vessel is preferably filled with the zeolites to from 70 to 90% of its volume.

After a certain period of operation, the zeolites are laden with impurities and the purification performance decreases. Regeneration (removal of the adsorbed impurities) is carried out in a customary fashion, e.g. by treatment of the zeolite bed with hot inert gases at from 200 to 400° C. for a number of hours. It is possible to arrange two or more zeolite beds next to one another (in parallel) and to pass the aromatic to be purified over one bed while the other bed is regenerated with hot inert gas.

The size of the adsorber, the type and amount of the zeolites and the flow velocity of the feed stream or the residence time in the absorber depend on the type and amount of the impurities, the purification performance required (tolerable concentration of impurities in the purified aromatic) and the desired regeneration cycles.

If the zeolites 1 and 2 are not used as a homogeneous mixture but instead are used separately from one another, the aromatic to be purified is preferably passed, viewed in the flow direction, firstly over the coarse-pored zeolite 2 and then over the fine-pored zeolite 1, i.e. the bed of zeolite 1 is arranged downstream of the bed of zeolite 2. However, in particular cases, the reverse order can also be advantageous.

Zeolite 2 can be installed upstream of zeolite 1 in a fixed bed in a simple manner by firstly introducing a layer of coarse-pored zeolite 2 into the adsorber and placing a second layer of fine-pored zeolite 1 on top of this first layer. The feed stream comprising impurities is then fed in at the bottom of the adsorber and taken off again in purified form at the top. In the case of the reverse order of zeolite 1 before zeolite 2, a layer of zeolite 1 is naturally introduced first and a layer of zeolite 2 is introduced on top of this.

The feed stream is preferably passed over the zeolites at a temperature of from 0 to 300° C., in particular from 50 to 200° C. and particularly preferably from 100 to 150° C., and a pressure of from 1 to 50 bar (absolute), in particular from 3 to 30 bar (absolute) and particularly preferably from 5 to 20 bar (absolute). Here, identical or different temperatures or pressures can be set for zeolite 1 and zeolite 2 or for the various zeolite beds, depending on the type and amount of the impurities and the purification performance required.

The aromatic to be purified is, for example, obtained by distillation from mixtures of aromatics or from a catalytic transformation of mixtures of aromatics known as hydrodealkylation. Typical impurities in the feed stream are therefore ones which are obtained in the extractive distillation of mixtures of aromatics, in particular N-methylpyrrolidone, N-formylmorpholine and sulfolane. Such nitrogen- or sulfur-comprising impurities can, for example, be determined by chemiluminescence or other analytical methods which those skilled in the art know to be suitable. The nitrogen content in the feed stream, calculated as $N_2$, is typically from about 0.1 to 10 ppm by weight, in particular from 0.5 to 5 ppm by weight, e.g. about 1 ppm by weight, per individual impurity and based on the unpurified aromatic, e.g. benzene. The performance of the catalyst is adversely affected even at concentrations of from 0.5 to 1 ppm of $N_2$.

The purification performance and thus the quality of the purification process according to the invention can most certainly be assessed by the behavior of the catalysts used in the polymerization or alkylation processes in which the aromatic which has been purified according to the invention is used further. The longer the life (period of operation) of these polymerization or alkylation catalysts, the lower the concentration of impurities in the starting materials and the better the purification performance of the purification process by means of which the starting materials have been purified beforehand.

The catalysts used in alkylation reactions in particular bind impurities very strongly and quickly become exhausted as a result of poisoning when the starting materials are not purified adequately. In the alkylation reaction, which is usually operated continuously, the catalyst is, for example, arranged as a fixed bed. In the case of a fresh catalyst, the reactive zone, i.e. the region within which the exothermic reaction (e.g. of benzene with ethylene to form ethylbenzene) occurs, is at the beginning of the fixed bed, viewed in the flow direction. As the period of operation increases, the reactive "hot" zone travels further along in the flow direction, since the beginning of the catalyst bed becomes increasingly laden with the impurities and thus deactivated, i.e. is no longer catalytically effective. When the reactive zone finally arrives at the end (outlet) of the fixed bed, the total amount of catalyst has become deactivated.

This effect can, for example, be measured by means of temperature measurements in the fixed catalyst bed: temperature measurement points located in succession along the fixed bed in the flow direction show the profile of the exothermic reaction over the fixed bed. If the temperature at the beginning of the fixed bed rises sharply, based on the temperature of the feed stream, a significant part of the conversion occurs here. If the temperature increase at the beginning of the fixed bed is small but that further downstream is high, the reaction has moved downstream. (If the temperature does not also increase at the end of the fixed bed, the catalyst bed is exhausted over its entire length and has to be replaced or regenerated.)

The purification process of the invention is more economical than the processes of the prior art. In particular, the polymerization and alkylation catalysts have a longer life when an aromatic which has been purified according to the invention is used. This considerably reduces the outlay for catalyst regeneration.

The invention further provides a process for preparing alkylated aromatics (alkylation process) by reacting aromatics and olefins over a catalyst, wherein the feed stream comprising aromatics is pretreated by the process of the invention according to any of claims 1 to 6 (purification process). Suitable catalysts are, in particular, Lewis acids or zeolites. Alkylation includes transalkylation.

Such alkylation processes are described, for example, in Ullmann, Encycl. of Industrial Chemistry, 5$^{th}$ Ed. Vol A10, pages 35 to 43. It is particularly preferably used in the zeolite-catalyzed alkylation or transalkylation of benzene and ethylene. Such processes and suitable catalysts are described, for example, in U.S. Pat. No. 5,902,917, U.S. Pat. No. 4,891,448, U.S. Pat. No. 5,081,323, U.S. Pat. No. 5,198,595, U.S. Pat. No. 5,243,116 or WO 98/07673.

In the alkylation process of the invention, preference is given to using benzene as aromatic and ethylene (so as to give ethylbenzene) or propylene (so as to give cumene) as olefin.

If zeolites are used as catalysts in the alkylation process, these are preferably different from the zeolites used in the purification process. Used catalysts can be employed as "guard bed".

In the alkylation of aromatics, it is advantageous to purify not only the aromatic feed stream but also the feed stream comprising olefin (or, in the case of transalkylation, other alkylaromatics). For example, both the benzene and the ethylene can be purified in the preparation of ethylbenzene. For this purpose, the olefin feed stream can, for example, be passed over a suitable adsorption bed as is described in WO 01/07383.

The process of the invention improves the purification of aromatics, in particular of aromatics which are to be used in a polymerization or alkylation process. The process prolongs the life of alkylation or transalkylation catalysts in the catalytic alkylation of aromatics by means of olefins, in particular over zeolite catalysts, and reduces the need for regeneration.

EXAMPLES

The following starting materials were used:
Zeolite 1: zeolite type Z4-04 from Zeochem, Switzerland, a zeolite having a mean pore size of 0.4 nm (4 Å) in the form of spheres having a diameter of from 2 to 3 mm, bulk density: about 730 kg/m$^3$
Zeolite 2: zeolite type Z10-03 from Zeochem, a zeolite having a mean pore size of 0.7 nm (7 Å) in the form of spheres having a diameter of from 1.6 to 2.3 mm, bulk density: about 650 kg/m$^3$
Benzene: benzene was dewatered azeotropically to a water content of less than 30 ppm by weight (measured by the Karl Fischer method in accordance with DIN 51777) in an upstream drying column
Ethylene: from the stream cracker of BASF in Ludwigshafen.

Example 1

For Comparison 20 t of the coarse-pored zeolite 2 were introduced into an adsorber tower having a diameter of 200 cm and a volume of 35 m$^3$ and distributed to form a fixed bed having a height of 10 m. Benzene was introduced continuously at the bottom of the adsorber tower and the purified benzene was taken off at the top of the tower. The mass flow of the benzene was 60-70 t/h, corresponding to a volume flow of 2 h$^{-1}$. The temperature of the benzene fed in was about 130° C.

The purified benzene obtained was mixed with ethylene in a mass ratio of 55:1 (benzene excess) and the mixture was passed through a fixed-bed reactor comprising a zeolite catalyst. The product obtained from this alkylation reaction was a mixture of unreacted benzene, ethylbenzene and multiply alkylated benzenes.

Four temperature sensors x1 to x4 were installed along the fixed-bed reactor used for the alkylation reaction, with x1 being located at the beginning of the fixed catalyst bed (entry of the reactants) and x4 at the end of the fixed bed (product exit). The sensors measured the increasing temperature ΔT of the reaction mixture in the fixed bed caused by the exothermic reaction. ΔT is based on the temperature of the feed stream.

The experiment was stopped after 4 weeks because the temperature increase ΔT at the beginning of the catalyst bed (x1) had decreased greatly and a drop in temperature at the end of the catalyst bed indicated that reaction was no longer complete. This indicated that the catalyst had become deactivated.

Example 2

According to the Invention

Example 1 was repeated, but 14 t of the coarse-pored zeolite 2 were firstly introduced into the adsorber tower and distributed to form a fixed bed having a height of 6.9 m, and 7 t of the fine-pored zeolite 1 were placed on top of this layer and distributed to form a fixed bed having a height of 3.1 m.

Otherwise, the procedure was as described in example 1, with the fixed-bed reactor for the alkylation reaction naturally comprising a fresh zeolite catalyst. The reaction could be carried out for 10 weeks without the catalyst becoming deactivated.

The table summarizes the results.

TABLE

Temperature increase ΔT at the sensors x1 to x4, based on the temperature of the feed stream (— means no measurement since the catalyst was exhausted at the beginning of the bed)

| | Week | | | | | | | | | | |
|---|---|---|---|---|---|---|---|---|---|---|---|
| | 0[1] | 1 | 2 | 3 | 4 | 5 | 6 | 7 | 8 | 9 | 10 |
| | ΔT (x1 = beginning of the catalyst bed) | | | | | | | | | | |
| Ex. 1 | 15.0 | 5 | 2.8 | 2 | 1.8 | — | — | — | — | — | — |
| Ex. 2 | 17 | 14.1 | 12.5 | 11.2 | 10.7 | 10.3 | 10 | 9.9 | 9.8 | 9.7 | 9.6 |

TABLE-continued

Temperature increase ΔT at the sensors ×1 to ×4, based on the temperature of the feed stream (— means no measurement since the catalyst was exhausted at the beginning of the bed)

| | Week | | | | | | | | | | |
|---|---|---|---|---|---|---|---|---|---|---|---|
| | 0[1] | 1 | 2 | 3 | 4 | 5 | 6 | 7 | 8 | 9 | 10 |
| ΔT (×2) | | | | | | | | | | | |
| Ex. 1 | 22.4 | 16 | 11.1 | 9.8 | 9 | — | — | — | — | — | — |
| Ex. 2 | 23.8 | 23.3 | 23 | 22.7 | 22.6 | 22.5 | 22.5 | 22.4 | 22.4 | 22.3 | 22.3 |
| ΔT (×3) | | | | | | | | | | | |
| Ex. 1 | 22.8 | 22.1 | 19.9 | 18.2 | 17.2 | — | — | — | — | — | — |
| Ex. 2 | 24.1 | 24.1 | 24.1 | 24.1 | 24.1 | 24.1 | 24 | 24 | 24 | 24 | 24 |
| ΔT (×4 = end of the catalyst bed) | | | | | | | | | | | |
| Ex. 1 | 23.2 | 23.2 | 23.2 | 23.2 | 22.9 | — | — | — | — | — | — |
| EX. 2 | 24.4 | 24.4 | 24.4 | 24.4 | 24.4 | 24.4 | 24.4 | 24.3 | 24.3 | 24.3 | 24.3 |

[1] Starting point

The examples show that in the case of comparative example 1, the catalyst at the beginning of the fixed catalyst bed (x1) was exhausted after a period of operation of only 4 weeks, since virtually no temperature increase ΔT was measurable in this region.

In example 2 according to the invention, the temperature increase at the beginning of the catalyst (x1) was still 40% of the temperature increase measured at the end of the catalyst (x4) after a period of operation of 10 weeks; the temperature increase measured at the end of the catalyst (x4) is the maximum possible temperature increase. Even at the measurement point x2, ΔT was still 90% of the maximum increase ΔT at the measurement point x4 after 10 weeks.

The purification process of the invention increased the life of the catalyst considerably.

What is claimed is:

1. A process comprising:
    (a) providing a process feedstream comprising an aromatic component; and
    (b) bringing the process feedstream into contact with a first zeolite and a second zeolite;
    wherein the first zeolite has a mean pore size of 0.3 to 0.5 nm, and wherein the second zeolite has a mean pore size of 0.6 to 0.8 nm.

2. The process according to claim 1, wherein the aromatic component comprises benzene.

3. The process according to claim 1, wherein the first zeolite is present in an amount of 30 to 70% by weight, and wherein the second zeolite is present in an amount of 30 to 70% by weight, based on a combined total weight of the first zeolite and the second zeolite.

4. The process according to claim 2, wherein the first zeolite is present in an amount of 30 to 70% by weight, and wherein the second zeolite is present in an amount of 30 to 70% by weight, based on a combined total weight of the first zeolite and the second zeolite.

5. The process according to claim 1, wherein the first zeolite has a mean pore size of 0.38 to 0.42 nm.

6. The process according to claim 1, wherein the second zeolite has a mean pore size of 0.68 to 0.72 nm.

7. The process according to claim 1, wherein the first zeolite has a mean pore size of 0.38 to 0.42 nm, and wherein the second zeolite has a mean pore size of 0.68 to 0.72 nm.

8. The process according to claim 2, wherein the first zeolite has a mean pore size of 0.38 to 0.42 nm, and wherein the second zeolite has a mean pore size of 0.68 to 0.72 nm.

9. The process according to claim 3, wherein the first zeolite has a mean pore size of 0.38 to 0.42 nm, and wherein the second zeolite has a mean pore size of 0.68 to 0.72 nm.

10. The process according to claim 1, wherein the first zeolite and the second zeolite each independently comprise a neutral zeolite.

11. The process according to claim 2, wherein the first zeolite and the second zeolite each independently comprise a neutral zeolite.

12. The process according to claim 3, wherein the first zeolite and the second zeolite each independently comprise a neutral zeolite.

13. The process according to claim 7, wherein the first zeolite and the second zeolite each independently comprise a neutral zeolite.

14. The process according to claim 1, wherein the first zeolite and the second zeolite are present in a fixed bed.

15. The process according to claim 1, wherein the process feedstream is contacted with the first zeolite and the second zeolite at a temperature of 50 to 200° C. and a pressure of 1 to 50 bar.

16. The process according to claim 2, wherein the process feedstream is contacted with the first zeolite and the second zeolite at a temperature of 50 to 200° C. and a pressure of 1 to 50 bar.

17. The process according to claim 3, wherein the process feedstream is contacted with the first zeolite and the second zeolite at a temperature of 50 to 200° C. and a pressure of 1 to 50 bar.

18. The process according to claim 7, wherein the process feedstream is contacted with the first zeolite and the second zeolite at a temperature of 50 to 200° C. and a pressure of 1 to 50 bar.

19. A process comprising:
    (a) providing a process feedstream comprising benzene; and
    (b) bringing the process feedstream into contact with a fixed bed comprising a first neutral zeolite and a second neutral zeolite, at a temperature of 50 to 200° C. and a pressure of 1 to 50 bar;
    wherein the first neutral zeolite has a mean pore size of 0.38 to 0.42 nm and is present in an amount of 30 to 70% by weight, and wherein the second neutral zeolite has a mean pore size of 0.68 to 0.72 nm and is present in an amount of 30 to 70% by weight, based on a combined total weight of the first neutral zeolite and the second neutral zeolite.

20. A process comprising:
(a) providing a feedstream comprising an aromatic component;
(b) bringing the feedstream into contact with a first zeolite and a second zeolite, wherein the first zeolite has a mean pore size of 0.3 to 0.5 nm, and wherein the second zeolite has a mean pore size of 0.6 to 0.8 nm, to form a pretreated feedstream; and
(c) reacting the pretreated feedstream with an olefin in the presence of a catalyst.

* * * * *